United States Patent
Laursen

(10) Patent No.: US 6,429,192 B1
(45) Date of Patent: Aug. 6, 2002

(54) PURIFICATION PROCESS FOR PRODUCTION OF MANNAN-BINDING LECTIN AND AN MBL MEDICINAL PRODUCT

(75) Inventor: Inga Laursen, Hellerup (DK)

(73) Assignee: Statens Serum Institut, Copenhagen (DK)

( * ) Notice: Subject to any disclaimer, the term of this patent is extended or adjusted under 35 U.S.C. 154(b) by 0 days.

(21) Appl. No.: 09/329,247

(22) Filed: Jun. 10, 1999

Related U.S. Application Data

(60) Provisional application No. 60/101,007, filed on Sep. 18, 1998.

(30) Foreign Application Priority Data

Jun. 10, 1998 (DK) .......................................... 1998 00793

(51) Int. Cl.$^7$ ............................................. A61K 38/16
(52) U.S. Cl. ........................... 514/8; 514/8; 424/178.1; 424/134.1; 530/350; 530/402; 530/391.7; 435/69.1; 435/235.1; 435/172.3; 435/91; 435/320.1
(58) Field of Search ............................ 435/69.1, 235.1, 435/172.3, 91, 320.1; 530/350, 391.7, 402; 536/27; 514/8; 424/134.1, 178.1

(56) References Cited

U.S. PATENT DOCUMENTS 5,270,199 A  12/1993  Ezekowitz .................. 435/69.1

OTHER PUBLICATIONS

Scand. J. Immunol. (1998) 48, 116–123, Valdimarssson et al "Reconstitution of Opsonizing Activity by Infusion of Mannan–Binding Lectin (MBL) . . . "
Immunology (Dec. 1995) 86, Supplement 1, (Joint Congress of the British and Netherlands Societies for Immunology) Abstract IS86.
The World of Pharmacia Biotech '95 '96 (Molecular Biology, Cell Biology, Chromatography, Electrophoresis and Spectrophotometry) 319–320.
Chemical Abstracts 121(21), Nov. 21, 1994, Abstract No. 253577; Dlabac, Vladimir et al. "Mannan–binding protein–like activity in the sera of newborn piglets" in Immunobiol. (Stuttgart) 190 (4–5) (1994), 399–410.
Joint Congress of the BSI and the NVVI, Collectins, 100, IS86 "Mannan–binding."
Biochem J (1996) 319, 329–32, Tan et al, "Improvements on the purification . . . "
Biochim Biophys Acta 883 (1986) 197–206, Summerfield et al, "Mannose–binding."
Transfusion Med 1997, 7, 289–94, Kilpatrick, "Isolation of human mannan . . . "
J Exp Med 169, Jan. 1989, 185–96, Ezekowitz et al, "A human serum mannose . . . "
Immun Today 17(11), Nov. 1996, 532–40, Turner, "Mannose–binding lectin . . . "
Protein Sci (1994), 3:1143–58, Hoppe et al. "Collectins–soluble proteins . . . "
Biochem Biophys Res Comm, 183(2) Mar. 16, 1992, 645–51, Matsushita et al, "Human mannose–binding protein . . . "
Nature 386(6624) Apr. 3, 1997, 506–10, Thiel et al. "A second serine . . . "
Human Reprod 10(9) 1995, 2501–05, Kilpatrick et al, "Association between . . . "
J Biochem 94(3) 1983, 937–47, Kawasaki et al, "Isolation and characterization."
J Immunol 144(6), Mar. 15, 1990, 2287–94, Lu et al, "Binding of the pentamer/hexamer forms . . . "
Methods Enzymology 179, 1989, 310–21, Kawasaki et al. "Mannose/N–acetylglucosamine–binding . . . "
Arch Biochem Biophys 283(1) Nov. 15, 1990, 217–22, Kyogashima et al, "Glycosphingolipid–binding specificity . . . "
J Am Chem Soc 68, Mar. 1946, 459–75, Cohn et al "Preparation and properties . . . "
Vox Sang 7, 1962, 414–24, Kistler et al "Large scale production . . . "
J Chromatography B: Biomed Appl 662(1994) 191–96 Koppel et al "Affinity purification of a mannose–binding . . . "

*Primary Examiner*—Karen Cochrane Carlson
*Assistant Examiner*—Hope A. Robinson
(74) *Attorney, Agent, or Firm*—Birch Stewart Kolasch & Birch, LLP.

(57) ABSTRACT

The starting material for the present purification process is a supernatant, suspension, milk product, colostrum or crude plasma protein fraction containing MBL. The starting material is subject to few pre-processing steps in order to obtain an MBL containing solution. By this it is possible to perform an affinity chromatography as the first chromatographic process step employing a non-conjugated polysaccharide matrix, from which MBL of a high purity is eluted. Besides constituting the major purification step of the process, the affinity chromatography also serves as a virus-removal step. In the production process of a virus-safe product, a virus-inactivation step is also included. The product of the process of the present invention is ready for use as medicinal product.

30 Claims, No Drawings

PURIFICATION PROCESS FOR PRODUCTION OF MANNAN-BINDING LECTIN AND AN MBL MEDICINAL PRODUCT

Priority of Application No. PA 1998 00793 filed in Denmark on Jun. 10, 1998 is claimed under 35 U.S.C. § 119. This application is based on provisional application No. 60/101,007 filed Sep. 18, 1998.

FIELD OF INVENTION

The present invention relates to a novel purification process for production of mannan-binding lectin (MBL) (formerly designated mannan binding protein, MBP) preferably from donor plasma, to be used as an MBL medicinal product. The product is to be used for substitution or replacement therapy in patients with inherited or acquired MBL-deficiency associated with functional and/or clinical symptoms, i.e. where it is contemplated that said patients would benefit from the administration of MBL, e.g. for the treatment or prevention of infections.

INTRODUCTION

Innate (also named natural or non-anticipatory) immune functions have recently received an increasing interest as important elements in defence mechanisms against potentially pathogenic microorganisms. Thus, attention has especially been given to a group of lectins, the collecting, which are believed to play an important role in the immediate defence against a wide range of microorganisms. The serum protein MBL is a collectin, i.e. it is built up as oligomeric structures, characterized by calcium-dependent, C-type carbohydrate-recognition domains (CRDs) attached to collagenous rods. The precise oligomerization of circulating MBL remains unclear; however, higher order oligomeric, bouquet-like structures such as hexameric MBL with multiple binding sites appear to be essential for the functional activity of MBL (for recent reviews, see references 1, 2) (a list of references is given at the end of this specification).

The cumulative knowledge about MBL indicates a future role for this protein in interventional therapy against serious infections. MBL is structurally similar to the complement component C1q, an essential component in the activation of the classical pathway of complement. MBL appears to activate the complement system by a mechanism analogous to that of C1q, i.e. via associated serine proteases, termed MASPs (MBL-associated serine proteases). This antibody-independent complement activation has been named the "MB-lectin pathway of complement activation" (3, 4).

MBL binds to carbohydrate structures on surfaces of bacteria, yeast, parasitic protozoa and viruses, and has been found to exhibit antibacterial activity through killing of the bacteria via the terminal, cytolytic pathway of the complement system, or through promotion of phagocytosis by opsonization. The level of MBL in plasma is genetically determined. Each individual has a constitutional MBL level reflected by the genomic structure in the controlling region as well as in the coding region. The concentration of MBL in plasma thus varies from about 10 µg/ml to less than 10 ng/ml. Infants or adults with deficiency or very low levels of MBL are especially susceptible to infections. Recent information points to a role of MBL deficiency as a susceptibility factor in HIV infection, and also to MBL deficiency being associated with more rapid death following development of AIDS (1). MBL deficiency may also predispose to recurrent spontaneous abortions (5).

Mannan-binding lectin was first isolated from human serum in 1983 (6) by affinity chromatography on mannan-Sepharose (mannan coupled to a Sepharose matrix) in the presence of Ca-ions. Elution of MBL from the affinity column was performed by means of EDTA.

It appears from later publications that MBL has been purified essentially by the same procedure from serum and plasma. The purified MBL preparations recovered from this one-step procedure were heavily contaminated by antibodies with specificity for carbohydrates and serum amyloid p-component (SAP). To obtain MBL of higher purity, further chromatographic steps were included in the purification procedures, such as a Sepharose precolumn to the affinity column, and additional affinity steps using different carbohydrates either coupled to the matrix or added to the elution buffer; other chromatographic principles as ion exchange and gel filtration chromatography were employed as well (7, 8, 9, 10). In general, at least two affinity chromatographic steps have been employed in the procedures for obtaining highly purified MBL. Recently a procedure has been described, where a plasma protein fraction obtained by precipitation of human plasma with 7% PEG was used as the starting material for MBL purification (11). This procedure differed from those previously described in that the affinity chromatography was performed on non-conjugated Sepharose (Sepharose without immobilized carbohydrate-ligands): first the solubilized PEG-precipitate was subjected to batch adsorption on Sepharose, and after elution of MBL by EDTA, a subsequent affinity chromatography step on a Sepharose column was performed, with eluting of MBL by mannose. By this procedure employing two consecutive affinity steps, MBL was obtained at high purity. DNA encoding human mannose binding protein is disclosed in WO98/01519.

DETAILED DISCLOSURE OF THE INVENTION

The present invention relates to a process for purifying mannan-binding lectin (MBL), preferably from a crude plasma protein fraction. The process of the invention will, among other elements, include at least two key elements: performing one affinity chromatography step on a non-conjugated polysaccharide matrix, and performing at least one validated virus-reduction step.

MBL can be purified from a wide range of starting materials containing MBL. In one embodiment, the starting material for the process of the invention is an MBL containing supernatant or a lysed cell suspension from a yeast or mammalian cell culture expressing MBL, said cell culture comprising cells coding for mammalian (e.g. human) MBL and optionally coding for the MBL Associated Serine Proteases (MASPs). The MBL expressing cell culture is grown in a medium providing the cell culture the nutrients needed with or without serum added to the culture medium. In another embodiment, MBL is purified from milk and/or colostrum from a mammal expressing a mammal (e.g. human) MBL gene. In one embodiment, the mammal is a transgenic non-human animal. In a preferred embodiment of the invention, the starting material for the process of the invention is a crude plasma protein fraction obtainable from industrial scale ethanol fractionation procedures, such as Cohn fraction I, II and III; Cohn fraction II and III; or Cohn fraction III. In a preferred embodiment, the plasma protein fraction is Cohn fraction II and III, where filter aid may or may not be present depending on the method employed for isolation of the Cohn fraction, i.e. by filtration or centrifugation. The use of Cohn fraction II and III as starting material has several advantages. These comprise, but are not limited to: no need of further ethanol fractionation, immunoglobulins can be recovered for an immunoglobulin product, and MBL is recovered from a fraction usually discarded.

Each of the starting materials will require a few pre-processing steps to obtain an MBL containing solution. The pre-processing steps will be discussed below.

The first key element of the present process, the affinity chromatography on a non-conjugated polysaccharide matrix, has several advantages. These comprise, but are not limited to: no need for prior protein precipitation, selectivity for functionally active MBL, a high degree of purification, removal of viruses, concentration by volume reduction.

The MBL containing solution is a complex protein mixture, where MBL may constitute less than 0.05% of the total proteins from the starting materials. Purification by means of chromatographic methods alternative to affinity chromatography would require further protein fractionation of the MBL containing solution e.g. by protein precipitation. The advantage of employing an affinity step is that no prior protein fractionation steps, such as precipitation and resuspension steps are needed, thus allowing the MBL containing solution to be applied directly to the column.

As a consequence of the pre-processing steps, e.g. the ethanol fractionation or the nature of the MBL expression system used, it is expected that the MBL containing solution contains MBL as native, oligomeric proteins as well as denatured and structurally impaired protein forms. Since the MBL product for use in medicine has to be constituted by functionally active MBL, it is of great importance to perform a purification step which selects for functionality. Affinity chromatography fulfils this requirement by selecting for functionally active, oligomeric ligand-binding MBL.

It is well known that affinity chromatography is the method of choice for purifying proteins from a complex protein mixture often resulting in several thousand fold of purification. By the affinity chromatography step of the present invention MBL is purified to a very high degree, i.e. more than 2500 fold. The affinity chromatography is the major purification step of the process, and contributes almost solely to the high purity obtained in the final MBL preparation of the process. Even purification to a minor degree is far beyond what is presently known in the art. Also, a purification which is 500 fold, i.e. 1000, 1500, 2000, or 2250 fold is acceptable. Purification to a minor degree is especially acceptable when less complex protein mixtures are used as the starting material. That is, if MBL constitutes more than about 0.05% of the total protein content.

Although the MBL containing solution applied to the column may have been concentrated, the concentration of MBL is still relatively low, and the affinity chromatography serves as a concentration step, by concentrating the MBL applied at least 3 fold, such as concentrating the MBL applied at least 4 fold.

The affinity chromatography step is performed on a non-conjugated polysaccharide based matrix. By a non-conjugated matrix is understood that no carbohydrate-ligands are coupled to the matrix. The advantages comprise, but are not limited to: The basic structure of the media used as matrix consists of bundles of polysaccharide chains, which act as ligands for MBL. There is no need for a special manufacturing of a matrix by chemically coupling of carbohydrate-ligands. Problems with an unstable matrix and/or uncontrolled leakage of ligands are avoided.

Furthermore, the matrix should preferably be cross-linked. The advantage of a cross-linked polysaccharide material is the rigidity and high physical stability, enabling the use of a large column with good flow properties in the process. The cross-linked matrix further has the advantage of a high chemical stability, enabling cleaning of the column with e.g. strong alkaline solutions. Preferred materials for the affinity chromatography step are gel materials containing agarose and/or dextran and/or cellulose such as Sepharose CL6B (Pharmacia), Ultrogel (Pharmacia), Bio-gel A materials, e.g. 0.5 m, 1.5 m, 15 m, and 50 m (all Bio-Rad), Sephadex gel materials, e.g. G-50, G-75, G-100, G-150, and G-200 (all Pharmacia), Sephacryl HR gel materials, e.g. S-300, S-400, S-500 (all Pharmacia), Superdex 200 prep grade (Pharmacia), Superose 6 prep grade (Pharmacia), and Cellulose gel material from Whatman, especially preferred materials for the affinity chromatography step is Sepharose CL4B (Pharmacia)

Preferably, the column is cleaned with 0.5 M NaOH in order to ensure aseptic production conditions and avoid batch-to-batch contamination. A person skilled in the art will appreciate the advantage of this cleaning procedure and the use of a matrix material for many cycles of chromatography.

After application of the MBL-containing solution to the affinity matrix, the column is washed. The buffers used for washing out protein contaminants from the affinity matrix are non-denaturing buffers having a composition, pH, and ionic strength resulting in elimination of the major proportion of protein contaminants without substantial elution of MBL. Initially, an equilibration buffer is used. This buffer could be a Tris buffer with a molarity within the range of 10–40 mM, preferably 10 mM, and a pH of 7.0–8.0, preferably 7.3, with a content of NaCl ranging from 100–250 mM, preferably 145 mM; and a content of $CaCl_2$ of 3–15 mM, preferably 5 mM. Subsequently a buffer with a low content of $CaCl_2$ is used. The low content of $CaCl_2$ could be 0.2–2.0 mM, preferably 0.3–1.0 mM, such as 0.5 mM. Due to the employment of a matrix to which MBL binds with high affinity in a $Ca^{2+}$-dependent manner, the concentration of $CaCl_2$ can be lowered in the washing buffer after a stable adsorption of MBL to the matrix has been established without substantial elution of MBL. In this manner, contaminants binding $Ca^{2+}$-dependently to the matrix with lower affinity, e.g. carbohydrate specific antibodies, are washed out.

The binding capacity of the column is defined as the total amount of MBL absorbed to and eluted from the matrix (calculated as volume of the eluate fraction times the concentration) divided by the volume of the gel-matrix. It is preferred that the binding capacity of the column is more than 20 µg MBL/ml packed matrix, e.g. more than 25 µg MBL/ml packed matrix, such as more than 30 µg MBL/ml packed matrix, more than 35 µg MBL/ml packed matrix, more than 40 µg MBL/ml packed matrix, more than 42 µg MBL/ml packed matrix, more than 44 µg MBL/ml packed matrix, more than 46 µg MBL/ml packed matrix, more than 48 µg MBL/ml packed matrix or even more than 50 µg MBL/ml packed matrix.

After washing the affinity chromatography column, the elution of MBL is performed with a selective desorbing agent in a neutral non-denaturing buffer capable of efficient elution of MBL. This buffer could be a Tris buffer with a molarity within the range of 10–40 mM, preferably 15 mM; and a pH of 7.0–8.0, preferably 7.3, with a content of NaCl ranging from 100–250 mM, preferably 100 mM. The desorbing agent could be a saccharide such as N-acetylglucosamine, mannose, N-acetylmannosamine or fucose and/or an agent chelating Ca-ions such as ethylene diamine tetra-acetic acid (EDTA). Optionally mannose is used, with a concentration within the range of 20–100 mM mannose, preferably 30 mM.

The second key element in the present process is performance of at least one validated virus-reduction step.

When discussing virus reduction steps, it is understood that a virus reduction step can be either a virus removal step and/or a virus inactivation step. More than one (e.g. two) virus removal steps and/or virus inactivation steps may be included in the present process.

The aim of validating a production step as a virus reduction step is to provide evidence that the production process will effectively inactivate/remove viruses which are either known to contaminate the starting materials, or which could conceivably do so. Validation studies involve the deliberate addition of a virus prior to the production steps to be validated and measuring the extent of its removal/inactivation after the production step or steps. GMP restraints prevent the deliberate introduction of any virus into the production facilities. Therefore, the validation should be conducted in a separate laboratory equipped for virological work on a scaled-down version of the production step and performed by staff with virological expertise in conjunction with the production engineers. The amount of virus added to the starting material for the production step which is to be validated should be as high as possible in order to determine the capacity of the production step to inactivate/remove viruses adequately. However, the virus spike should be added such that the composition of the production material is not significantly altered. Preferably, the volume of the virus spike will be equal to or less than 10%.

Quantitative infectivity assays should be performed according to the principles of GLP and may involve plaque formation, detection of other cytopathic effects such as syncytia or foci formation, end point titration (eg., $TCID_{50}$ assays), detection of virus antigen synthesis or other methods. The method should have adequate sensitivity and reproducibility and should be performed with sufficient replicates and controls to ensure adequate statistical accuracy of the results.

Typically, a process step is challenged with 6 logs of virus, and if a reduction in the order of 4 logs or more is acquired, it is indicative of a clear effect with the particular test virus under investigation. Similarly, a reduction in the order of 4.5 logs, 5 logs, or even 5.5 logs, is indicative of a clear effect with the particular test virus under investigation, and the step can be classified as a validated virus reduction step The virus validation studies should be performed with viruses resembling those which may contaminate the product as closely as possible and secondly to represent as wide a range of physico-chemical properties as possible in order to test the ability of the system to eliminate viruses in general.

Validation studies have shown that the present affinity chromatography step functions as a removal step for non-enveloped viruses and will be expected to remove enveloped viruses as well by a partition process. By this, the affinity chromatography constitutes a first virus reduction step in the present process (see example 4).

In a preferred embodiment, the validated virus reduction step is a virus inactivation step. Infectious enveloped viruses are preferably inactivated by addition of a virucidal amount of virus-inactivating agent to the MBL-containing eluate recovered from the affinity chromatography step. A "virucidal amount" of virus-inactivating agent is intended to denote an amount giving rise to a solution in which the virus particles are rendered substantially non-infectious, and by this a virus-safe MBL-containing solution is obtained. Such "virucidal amount" will depend on the virus-inactivating agent employed as well as the conditions such as incubation time, pH, temperature, content of lipids, and protein concentration.

The term "virus-inactivating agent" is intended to denote such an agent or a method which can be used in order to inactivate enveloped viruses as well as non-enveloped viruses. The term "virus-inactivating agent" is to be understood as encompassing both a combination of such agents and/or methods, whenever that is appropriate, and only one type of such agent or method.

Preferred virus-inactivating agents are detergents and/or solvents, most preferably detergent-solvent mixtures. It is to be understood that the virus-inactivating agent is optionally a mixture of one or more detergents with one or more solvents. Solvent/detergent (S/D) treatment is a widely used step for inactivating enveloped viruses (e.g. HIV1 and HIV2, hepatitis C and non A-B-C, HTLV1 and HTLV2, the herpes virus family, including CMV and Epstein Barr virus) in plasma derived products. A wide variety of detergents and solvents can be used for virus inactivation. The detergent may be selected from the group consisting of non-ionic and ionic detergents, and is selected to be substantially non-denaturing. Preferably, a non-ionic detergent is used as it facilitates the elimination of the detergent from the MBL preparation in the subsequent step. Suitable detergents are described, e.g. by Shanbrom et al., in U.S. Pat. No. 4,314,997, and U.S. Pat. No. 4,315,919. Preferred detergents are those sold under the trademarks Triton X-100 (t-octylphenoxypolyethoxyethanol) and Tween 80 (polysorbat 80) which may be used solely or in combination. Preferred solvents for use in virus-inactivating agents are di- or trialkylphosphates as described e.g. by Neurath and Horowitz in U.S. Pat. No. 4,764,369. A preferred solvent is tri(n-butyl)phosphate (TNBP). An especially preferred virus-inactivating agent for the practice of the present invention is a mixture of TNBP and Tween 80, but, alternatively, other combinations can be used. The preferred mixture is added in such a volume that a concentration of TNBP in the solution is within the range of 0.2–1.0% by weight, preferably at a concentration of about 0.3% by weight. The concentration of Tween 80 in the solution is within the range of 0.8–1.5% by weight, preferably at a concentration of about 1% by weight.

The virus-inactivation step is conducted under conditions inactivating enveloped viruses resulting in a substantially virus-safe MBL-containing solution. In general, such conditions include a temperature of 4–30° C., such as 19–28° C., 23–27° C., preferably about 25° C. incubation time found to be effective by validation studies. Generally, an incubation time of 1–24 hours is sufficient, preferably 4–12 hours, such as about 6 hours to ensure sufficient virus inactivation. However, the appropriate conditions (temperature and incubation times) depend on the virus-inactivating agent employed, pH, and the protein concentration and lipid content of the solution.

Validation studies of the present S/D treatment is presented in example 4.

It is contemplated that other methods for removal of or inactivating virus can also be employed to produce a virus-safe MBL product, such as the addition of methylene blue with subsequent inactivation by radiation with ultraviolet light.

In one aspect of the invention the affinity chromatography is a validated virus reduction step such that the two key elements are performed as one.

The preferred process for production of MBL from a crude MBL-containing plasma protein fraction contains the steps outlined below:

Step a) preparing an aqueous suspension of the crude MBL-containing protein fraction at acidic pH and substantially non-denaturing temperature, Step b) eliminating the majority of immunoglobulins from the suspension of step a) and recovering an MBL-containing protein fraction, Step c) solubilizing the MBL-containing fraction of step b., extracting MBL at neutral pH, and recovering an MBL-containing solution, Step d) adding a mixture of a solvent and a detergent to the MBL-containing solution from step c), Step e) applying the said MBL-containing solution of step d) to a non-conjugated polysaccharide based matrix under conditions promoting the binding of MBL to the matrix, Step f) washing out protein contaminants from said polysaccharide based matrix of step e) with a non-denaturing buffer and/or buffers having a composition, pH, and ionic strength resulting in elimination of the major proportion of protein contaminants without substantial elution of MBL, Step g) eluting MBL from the polysaccharide based matrix of step f) with a selective desorbing agent in a neutral non-denaturing buffer with efficient elution of MBL, which yields an MBL-containing eluate, Step h) adding a virucidal amount of a non-denaturing virus-inactivating agent to the MBL-containing eluate of step g) resulting in a substantially virus-safe MBL-containing solution, Step i) applying the MBL-containing solution of step h) onto an anion exchange matrix under conditions whereby MBL binds to the matrix, Step j) washing the anion exchange matrix of step i) with a buffer having an ionic strength and pH sufficient to wash out the virus-inactivating agent from the matrix without causing substantial elution of MBL, Step k) eluting MBL from the anion exchange matrix of step j) with a substantially non-denaturing buffer having an ionic strength and pH sufficient to cause efficient elution of MBL, which yields an MBL-containing eluate, Step l) subjecting the MBL-containing eluate fraction of step k) to ultrafiltration, by this recovering an MBL-containing concentrate, Step m) subjecting said MBL-containing concentrate of step l) to gel filtration chromatography, by this recovering an MBL-containing solution of functionally active, oligomeric MBL proteins in a non-denaturing physiological buffer.

Steps a)–c) are the pre-processing steps of the process for purifying MBL from a crude plasma protein fraction.

Steps e)–g) and step h) are described above as the key elements of the process of the present invention.

Step a) Thus, the first step of the present process for production of MBL from plasma is the preparation of an aqueous suspension of the precipitated Cohn fraction, with a subsequent elimination of the majority of immunoglobulins from said suspension, thereby recovering a substantially immunoglobulin free MBL-containing protein fraction. It is preferred that the precipitated Cohn fraction is suspended in water and/or buffer at a sub-stantially non-denaturing temperature and pH. The term "substantially non-denaturing" means that the condition to which the term refers does not cause substantial irreversible loss of functional activity of MBL nor of the immunoglobulins present. Advantageously, the plasma protein fraction is suspended in water acidified with at least one non-denaturing buffer system at volumes of from 6 to 9, preferably from 7 to 8, times that of the plasma protein fraction. The pH of the suspension is preferably maintained at a pH below 6, such as within the range of 4.0–6.0, preferably 5.1–5.7, most preferably about 5.4. Any suitable acidic buffer can be used, but the buffer system preferably contains at least one of the following buffers and acids: sodium phosphate, sodium acetate, acetic acid, HCI. Persons skilled in the art will appreciate that numerous other buffers can be used. The protein suspension is preferably maintained at a cold temperature, inter alia in order to prevent substantial protein denaturation and to minimize protease activity. The plasma protein suspension and water as well as the buffer system added preferably have the same temperature, within the range of 0–12° C., preferably 0–8° C., most preferably 1–4° C.

Step b) The MBL-containing non-solubilized protein material, termed the "residual paste" is isolated by means of depth filtration or by centrifugation. Preferably the suspension of the invention is filtered. The filtration is preferably performed through depth filters, e.g. C150 AF, AF 2000 or AF 1000 (Schenk), or similar filters. The majority of immunoglobulins in the suspension is eliminated by means of said filtration.

Step c) MBL is subsequently extracted from the residual paste under neutral conditions, preferably at a temperature from 1–8° C., after addition of an essentially non-denaturing buffer. The buffer for extraction is preferably a Tris-buffered saline (TBS), with a concentration of Tris from 10–40 mM, preferably 10 mM, with a pH of 7.5–9.0, preferably 8.5, and a NaCl concentration of 100–200 mM, preferably 140 mM. Skilled artisans will appreciate that other non-denaturing buffers can be used to extract MBL. The by extraction obtained MBL containing solution is recovered by filtration through series of depth filters with decreasing pore sizes and a delipid filter, preferably as described in Example 1. This MBL containing solution can advantageously be concentrated by means of ultrafiltration before the affinity chromatography step.

Step d) Before the MBL containing solution is applied to the affinity column, a mixture of solvent and detergent such as 0.8–1.5% Tween 80 and/or Triton X-100 and 0.2–1.0% TNBP, is preferably added to the solution, most preferably 0.3% TNBP and 1.0% Tween 80, to reduce the content of lipoproteins in the MBL containing solution eluted in the subsequent affinity chromatography step. As a consequence of the high content of lipid and lipoproteins in the solution, this solvent/detergent treatment will not constitute a virus-inactivation step of the art. However, it will be expected that a high proportion of enveloped viruses will be inactivated by said treatment.

Step i) When performing the ion exchange chromatography step for the purification of MBL, it is preferred that the conditions, e.g. the pH and ionic strength, are chosen in such a way that substantially all of the MBL present in the solution applied to the anion exchange matrix binds to the matrix. Virus-inactivating agent or agents are removed in the subsequent washing of the anion exchange matrix.

As will be known by the person skilled in the art, ion exchangers may be based on various materials with respect to the matrix as well as to the attached charged groups. For example, the following matrices may be used, in which the materials mentioned may be more or less cross-linked: agarose based (such as Sepharose CL-6B®, Sepharose Fast Flow® and Sepharose High Performance®), cellulose based (such as DEAE Sephacel®), dextran based (such as Sephadex®), silica based and synthetic polymer based. For the anion exchange matrix, the charged groups which are covalently attached to the matrix may e.g. be diethylaminoethyl (DEAE), quaternary aminoethyl (QAE), and/or quaternary ammonium (Q). Other anion exchangers can be used.

If, for instance, the chosen anion exchange matrix is Q Sepharose FF®, then the column is advantageously equilibrated with a non-denaturing alkaline buffer having about the same pH and ionic strength as the MBL solution to be loaded. Any of a variety of buffers are suitable for the equilibration of the ion exchange columns, e.g. sodium phosphate, tris(hydroxymethyl)amino-methane. Persons skilled in the art will appreciate that numerous other buffers may be used for the equilibration as long as the pH and conductivity are about the same as for the applied MBL solution. A preferred buffer for the equilibration of the anion exchange column is a Tris buffer having a Tris concentration within the range of 10–40 mM, such as within the range of 20–30 mM, preferably about 15 mM. It is preferred that the pH of the Tris buffer used for equilibration is within the range of 7.0 to 9.0, such as within the range of 7.5–8.5, preferably about 8.0. The buffer used preferably contains a concentration of NaCl in the range of 10–40 mM such as 20–30 mM preferably 25 mM NaCl.

Step j) The initial washing is advantageously performed by using the equilibration buffer, even though other buffers, with a similar concentration and pH-value may be used for the washing. The washing is performed with a volume 10–20 times that of the column volume.

Step k) The elution of the MBL from the anion exchange matrix is preferably performed with a substantially non-denaturing buffer having a pH and ionic strength sufficient to cause efficient elution of the MBL, thereby recovering an MBL-containing eluate. In this context, efficient elution means that at least 80%, such as at least 90%, e.g. at least 95% of the MBL proteins are loaded onto the anion exchange matrix. The elution is advantageously carried out with a Tris buffer containing 5–25 mM, such as 10–30 mM, preferably 15 mM Tris and 0.1–1.0 M such as 0.3–0.7 M, preferably 0.5 M NaCl, with a pH in the range of 6.0–9.0, such as 7.0–8.0, preferably 7.4.

It is preferred that the salt concentration of the eluting buffer is sufficiently high in order to displace the MBL from the matrix. However, it is contemplated that a decrease in pH and a lower salt concentration can be used to elute the MBL from the matrix.

Step l) Subsequent to elution from the anion exchange column, the eluate is preferably concentrated. The membranes employed for the ultrafiltration advantageously have a nominal weight cutoff within the range of 10,000–100,000 Da. A preferred membrane type for the present process is a membrane with a nominal weight cutoff of 100,000 Da, obtained from Sartorius. Other ultrafiltration membranes of comparable porosity may be employed.

Step m) The last chromatography step of the process, the gel filtration step, can be regarded as a polishing step, whereby SAP, lgG, protein aggregates, and structurally impaired MBL, which might have formed during the steps subsequent to the affinity chromatography, are eliminated.

The preferred process for production of MBL from an MBL containing lysed cell suspension or supernatant comprises at least the pre-processing step of filtering the MBL containing lysed cell suspension or supernatant to clarify the solution and remove e.g. cell debris.

After this pre-processing step whereby an MBL containing solution is obtained, steps d)–m) are performed as described above. In another embodiment, the process for production of MBL from an MBL containing lysed cell suspension or supernatant comprises the pre-processing step and steps e)–m).

The preferred process for production of MBL from an MBL containing milk product or colostrum contains the following pre-processing steps:

Step 1) adding a water soluble, substantially non-denaturating protein precipitant to the MBL containing milk product or colostrum in an amount sufficient to cause precipitation of a high proportion of non-MBL components, without causing substantial precipitation of MBL, or precipitation of the majority of MBL without causing substantial precipitation of non-MBL components; thereby forming a mixture of a solid precipitate and a liquid supernatant.

Step 2) recovering a clarified MBL-containing supernatant from the said mixture of step 1) or a clarified resuspended MBL-containing precipitate from the said mixture of step 1).

Step 1) Substantially non-denaturating, water-soluble protein precipitants are well known in the field of protein purification. Such precipitants are used for protein fractionation, resulting in partial purification of proteins from suspensions. Suitable protein precipitants for use in the process of the present invention include various molecular weight forms of PEG, caprylic acid, and ammonium sulphate. Those skilled in the art will appreciate that several other non-denaturating water soluble precipitants may be used as alternative means for the precipitation. The term "adding a protein precipitant" and variants of that term implies the addition of one or more types of protein precipitation agents.

Step 2) After completion of the protein precipitation, an MBL containing supernatant or solution of resuspended precipitate is recovered. The first part of the recovery is performed by conventional techniques for separating liquid from solid phase, such as centrifugation and/or filtration. Preferably, a flow-through centrifuge with 1000–5000 g force is used. In another embodiment the first part of the recovery is performed by a depth filtration on a filter press. The MBL containing supernatant is hereby recovered.

The precipitate containing the majority of MBL obtained by the first part of the recovery is resuspended by addition of non-denaturing neutral buffer.

Optionally, the recovered MBL containing supernatant or resuspended precipitate is depth filtered to remove larger particles and aggregates. This is optionally followed by sterile filtration performed by use of a conventional sterilization filter (such as a 0.22 $\mu$m filter from Millipore or Sartorius), which eliminates e.g. bacteria from the solution.

After the pre-processing steps 1) and 2) whereby an MBL containing solution is obtained, the preferred process for production of MBL from an MBL containing milk product or colostrum proceeds with steps d)–m) as described above.

The process of the invention is optimized to obtain a high yield of MBL with a high purity (see Example 3). The yield of the process of the present invention is calculated as the percent of the amount of MBL in the final product releative to the mean amount of MBL in the MBL containing solution applied to the affinity chromatography column. This yield is more than 40%, which is considered to be satisfactory, especially with the concomitant purity of the final MBL preparation prior to formulation, with MBL constituting about 60% of the total proteins. With other starting material also lower yields may be acceptable. Preferably the yield is at least 20%, such as 25%, 30%, 35%, 40% or even more than 40%.

The prior art procedures described in the introduction section have all been performed in small laboratory scale with the aim to obtain MBL for analytical research, i.e. employing up to about 1 litre of plasma as a starting material. The present invention aims at producing mannan-binding lectin in large production scale. By "large production scale" is, when a crude plasma protein fraction is the starting material, understood that the starting material preferably is a plasma pool from more not fewer than 1,000 donors. Another, more general, conception of "large production scale" is a binding capacity of the column in the first key step of more than 20 $\mu$g MBL/ml packed matrix, e.g. more than 25 $\mu$g MBL/ml packed matrix, such as more than 30 $\mu$g MBL/ml packed matrix, more than 35 $\mu$g MBL/ml packed matrix, more than 40 $\mu$g MBL/ml packed matrix, more than 42 $\mu$g MBL/ml packed matrix, more than 44 $\mu$g MBL/ml packed matrix, more than 46 $\mu$g MBL/ml packed matrix, more than 48 $\mu$g MBL/ml packed matrix or even more than 50 $\mu$g MBL/ml packed matrix.

The process of the present invention further aims at purifying MBL from a cell culture supernatant, from a lysed cell suspension, a milk product, or colostrum for subsequent use of the MBL product as a medicinal product in humans. Hence, the manufacturing process has to comply with requirements stated in Directives and guidelines from EEC to medicinal products such as biotechnological/biological products or products derived from human plasma, e.g. Note for guidance on plasma derived medicinal products, CPMP/BWP/269/95 or similar guidelines.

These requirements include, but are not limited to, the use of chemical agents in the purification process as well as in the final product. In the present process MBL is purified without the addition of protease inhibitors, such as PMSF, or bacteriostatic agents, such as azide and merthiolate. The product is thus totally free from added protease inhibitors and bacteriostatic agents.

The MBL product is manufactured according to GMP, under aseptic conditions in classified locations. To avoid proteolytic degradation of proteins during production, the process is mainly performed in cold rooms. The process of the invention is thus designed to produce an MBL product for use in medicine.

The MBL-product of the present purification process will, despite all efforts, contain other proteins than MBL. Using human plasma as the starting material plasma proteins such as IgM will be present.

It is of major importance for the clinical effect of the MBL product that the functional activity of MBL is maintained, i.e. the product is constituted by functionally active, oligomeric MBL. In this context a functionally active MBL is defined as an MBL capable of a) binding to carbohydrate on the surfaces of microorganisms (e.g. yeast mannan), b) by its ability to facilitate phagocytosis of MBL-bound microorganisms through interaction with collectin-receptors on phagocytic cells, and c) by its ability to activate complement as a consequence of binding to e.g. the surface of microorganisms. This activation of complement seems to occur via the MBL-associated serine proteases MASP 1 and 2, and elicits complement effector functions like inflammatory reactions, opsonisation, and cytolytic reactions.

MBL functional activity can be demonstrated in vitro by binding of MBL to mannan in mannan-coated ELISA-plates, a phagocytic assay where MBL-coated zymosan particles are ingested by phagocytic cells from peripheral blood, and by complement activation as visualised by deposition of complement factors (e.g. C3 or C4) after binding of MBL to carbohydrate in an ELISA-type assay.

In order to stabilize the MBL proteins during storage, the product is formulated by adding at least one protein stabilizing agent. Protein stabilizing agents are known to those skilled in the art, and include e.g. different sugar alcohols and saccharides (such as sorbitol, glucose, sucrose, trehalose, maltose), proteins (such as albumin), and amino acids (such as lysine, glycine). In the present invention albumin is preferred as a protein stabilizer, preferably at a concentration of 0.1–1% by weight, such as 0.5% by weight.

The MBL product is formulated as a liquid product for intravenous administration. An important aspect of the process of the invention is that the purified MBL becomes highly concentrated. It is thus possible to obtain a product with a concentration of at least 250 $\mu$g of MBL per ml. The high concentration of MBL increases the stability of the liquid product. The MBL product can also be lyophilized in order to increase stability over time. The concentration of the lyophilized product is calculated by following the guidelines given by the manufacturer for reconstitution of the lyophilized product.

The primary indications for the MBL product is congenital and acquired MBL deficiency. In addition the MBL product has several indications:

Neurology: Chronic inflammatory demyelinating polyneuropathy (CIDP, Multifocal motoric neuropathy, Multiple sclerosis, Myasthenia Gravis, Eaton-Lambert's syndrome, Opticus Neuritis, Epilepsy;

Gynaecology: Abortus habitualis, Primary antiphospholipid syndrome;

Rheumatology: Rheumatoid arthritis, Systemic lupus erythematosus, Systemic scleroderma, Vasculitis, Wegner's granulomatosis, Sjøgren's syndrome, Juvenile rheumatoid arthritis;

Haematology: Autoimmune neutropenia, Autoimmune haemolytic anaemia, Neutropenia;

Gastrointestinal: Crohn's disease, Colitis ulcerous, Coeliac disease;

Others: Asthma, Septic shock syndrome, Chronic fatigue syndrome, Psoriasis, Toxic shock syndrome, Diabetes, Sinuitis, Dilated cardiomyopathy, Endocarditis, Atherosclerosis, Adults with AIDS and bacterial infections, Primary hypo/agammaglobulinaemia including common variable immunodeficiency, Wiskot-Aldrich syndrome and severe combined immunodeficiency (SCID), Secondary hypo/agammaglobulinaemia in patients with chronic lymphatic leukaemia (CLL) and multiple myeloma, Children with AIDS and bacterial infections, Acute and chronic idiopathic thrombocytopenic purpura (ITP), Allogenic bone marrow transplantation (BMT), Kawasaki's disease, and Guillan-Barre's syndrome.

EXAMPLES

It is to be understood that the examples described below are illustrative of embodiments of the present process, and the invention is not intended to be so limited.

Example 1

PROCESS STEPS IN THE PURIFICATION OF PLASMA DERIVED MBL TO BE USED AS A MEDICINAL PRODUCT

All steps are performed at 5±3° C., except for step 5 which is performed at 25° C., and steps 7 and 8 which are performed at room temperature.

Step 1: Preparation of Cohn Fraction II+III Paste:

Cohn fraction II+III paste is prepared from human plasma by a standard Cohn fractionation procedure (12) essentially as modified by Kistler-Nitschmann (13). The ethanol precipitation is initiated after the cryoprecipitate has been removed and, if desired, after adsorption of certain plasma proteins (such as Factor IX and Antithrombin) to e.g. an ion exchange material and/or a Heparin Sepharose matrix. The exact conditions (pH, ethanol concentration, temperature, protein concentration) for obtaining the fraction II+III paste appear from the figure at page 266 in Harns JR (ed), Blood Separation and Plasma Fractionation, Wiley-Liss, New York, 1991. The paste is isolated on a filter press by adding filter aid prior to filtration.

Step 2: Extraction of Immunoglobulins from Cohn Fraction II+III Paste:

From 140 kg of fraction II+III paste including 30 kg of filter aid (Schenk, Germany) corresponding to a starting volume of plasma of about 1150 kg, extraction is accomplished by first adding 525 kg of 2.3 mM sodium phosphate/acetate buffer, pH 4.0, with slow stirring for about 1.5 hours, followed by 2 consecutive additions of 350 kg of water for injection (WFI), with stirring for about 1.5 hours after each addition. Finally, about 280 kg of 21.5 mM sodium phosphate/acetate, pH 7.0, are added, thereby adjusting the suspension to a final pH of 5.4. The suspension is filtered through a depth filter (C-150AF, Schenk, Germany). The filtrate contains among other proteins, the immunoglobulins, whereas MBL remains in the recovered residual paste.

Step 3: Preparation of an MBL Containing Solution

To the MBL-containing residual paste (constituting about 80 kg including filter aid) is added Tris-buffered saline, TBS (10 mM Tris, 140 mM NaCl), pH 8.4, in an amount equivalent to 3 kg per kg of residual paste. The suspension is stirred for about 16 hours to extract MBL. The suspension is filtered through a series of depth filters with decreasing pore sizes and a delipid filter: C-150-AF and AF-1000 filter plates (Schenk, Germany), and cartridges of 50LA, of 90LA, and of delipid filters (Cuno, France). The filtrated MBL containing solution is ultrafiltrated on a system employing membranes with a nominal weight cutoff value of 300 kDa (Sartorius, Germany), by this the solution is concentrated approximately 10 fold. The concentrated MBL containing solution is finally filtered through a 0.45 µm filter cartridge (Pall SLK 7002 NLZP, UK). Tri-n-butylphosphate (TNBP) and Tween 80 are added to the final solution to concentrations of 0.3% and 1.0% by weight, respectively. This mixture is stirred for 3.5 hours. Subsequently, $CaCl_2$ is added to a concentration of 5 mM followed by the addition of an equal volume of TBS containing 5 mM $CaCl_2$, pH 7.3.

Step 4: Affinity Chromatography on Sepharose CL4B:

A column is packed with 10 litres of Sepharose CL4B® (Pharmacia Biotech, Sweden) and equilibrated with TBS containing 5 mM $CaCl_2$ (10 mM Tris, 145 mM NaCl, 5 mM $CaCl_2$), pH 7.3. The MBL containing solution is applied to the column. Following application the column is successively washed with 3 column volumes of equilibration buffer and 6 column volumes of TBS containing 0.5 mM $CaCl_2$ (10 mM Tris, 200 mM NaCl, 0.5 mM $CaCl_2$), pH 7.3. MBL is eluted from the affinity column with TBS containing mannose (15 mM Tris, 100 mM NaCl, 30 mM mannose), and the eluted MBL fraction is recovered.

Step 5: S/D Treatment:

The mannose concentration of the eluted MBL fraction is adjusted to about 10 g/kg by adding 4.6 g of mannose per kg of eluate, then a filtration is performed through a combined 0.45 and 0.2 µm filter (Sartobran P Capsule, Sartorius, Germany). The filtrate is subsequently S/D treated by adding Tween 80 and TNBP to final concentrations of 1.0% and 0.3% by weight, respectively. The S/D treatment proceeds for at least 6 hours at 25° C.

Step 6: Removal of S/D by Anion Exchange Chromatography:

A column is packed with 600 ml of Q Sepharose FF® (Pharmacia Biotech, Sweden) and equilibrated with 15 mM Tris containing 25 mM NaCl, pH 8.0. The S/D treated MBL solution is diluted with a volume of 15 mM Tris, pH 8.0, 3 times that of the solution. The diluted MBL solution is applied to the anion exchange column, the column is subsequently washed with 10 column volumes of equilibration buffer, and MBL is eluted with 15 mM Tris containing 0.5 M NaCl, pH 7.4.

Step 7: Concentration by Ultrafiltration:

The eluted MBL fraction is diluted by adding 2 volumes of 15 mM Tris, pH 7.1, and subjected to concentration by ultrafiltration employing a Sartocon Micro UF System (Sartorius, Germany) with a 100 kDa nominal weight cutoff membrane. The concentrated solution containing 5 to 7 mg of MBL/ml is filtered through a combined 0.45 and 0.2 µm filter (Sartobran 300, Sartorius, Germany), and adjusted to 3 mM EDTA by adding solid EDTA.

Step 8: Gel Filtration on Superose 6:

A column is packed with 4 litres of Superose 6 prep grade (Pharmacia Biotech, Sweden) and equilibrated with PBS (8 mM $Na_2HPO_4$, 1.4 mM $NaH_2PO_4$, 145 mM NaCl), pH 7.3. The EDTA adjusted and filtered MBL concentrate is applied to the column, and gel filtration is performed with PBS as buffer. The final MBL fraction elutes as the first major peak from the column and is collected.

Step 9: Formulation of the MBL as a Liquid Medicinal Product:

The final MBL fraction is a solution of MBL in a physiological buffer (PBS, pH 7.3) with a concentration ranging from 300 to 400 µg of MBL per ml. To this MBL solution the protein stabilizer albumin is added as a nano-filtered (through a 15 nm filter) solution to a concentration of 0.5% (w/v). The final albumin-stabilized MBL preparation is sterile filtered (Sartobran 300, Sartorius), and filled aseptically as 3 mg of MBL per portion in a volume of no more than 10 ml.

Example 2

ANALYTICAL METHOD TO QUANTIFY MBL IN THE PROCESS

Quantity determination of MBL by a specific ELISA:

MBL is quantified in an MBL specific sandwich ELISA. A mouse monoclonal anti-MBL antibody is used for catching and also for detection of MBL. In this assay, the detection antibody is biotinylated. After binding to the biotinylated antibodies, streptavidin-conjugated HRP converts the colour reagent OPD in a concentration-dependent manner. The concentration of the samples analysed are estimated by use of an MBL serum standard.

Example 3

YIELD FROM THE PURIFICATION PROCESS

The volume of the MBL containing solution prepared from 80 kg of residual paste makes a total of about 360 kg, with a concentration of about 1.7 mg of MBL per litre. The MBL containing solution is concentrated approximately 10 fold by ultrafiltration employing a membrane with a cutoff value of 300 kDa in order to have a volume easier to handle in the subsequent purification process and to eliminate a portion of proteins with lower molecular weight from the MBL containing solution. The final concentrated MBL containing solution with a mean volume of 38 kg, contains about 68 g of total protein and has a mean concentration of 14.6 mg of MBL per litre ($\rho$=1.011 kg/l). The total recovery from the extraction process results in about 550 mg of MBL, equivalent to 0.48 mg per kg of starting plasma, 3.9 mg per kg of paste II and III, and 6.9 mg MBL per kg of residual paste.

The concentrated MBL containing solution constitutes the material for the subsequent purification steps of the process starting with the affinity chromatography step. The yield of the purification process (Example 1) is about 235 mg of MBL corresponding to a recovery of about 43% of the MBL present in the solution. The purity of the final MBL preparation before formulation is high, MBL constitutes about 60% of the total protein content.

Example 4

VALIDATION OF VIRUS REDUCTION STEPS

The virus reduction steps were validated in accordance with the CPMP Note for Guidance on Virus Validation Studies: The Design, Contribution and Interpretation of Studies Validating the Inactivation and Removal of Viruses (CPMP/BWP/268/95) and Note for Guidance on Plasma Derived Medicinal Products (CPMP/BWP/269/95).

Validation of the S/D Treatment Step

The S/D treatment step of the purification process was validated for virus inactivation, Three enveloped viruses were selected for this study, bovine viral diarrhoea virus (BVDV), human immunodeficiency virus (HIV) and porcine pseudorabies virus (PRV). The choice of viruses reflects the viruses that may contaminate human blood and/or plasma and/or includes model viruses of these viruses.

Samples from the relevant stage of the production process were spiked with the viruses of choice and S/D treatment performed. Samples were collected and the amount of virus was quantified by assays in cell cultures. The virus clearance and reduction factors were then calculated. The results from the study are summarized as follows:

| S/D treatment step | BVDV | HIV | PRV |
| --- | --- | --- | --- |
| Virus clearance factor ($\log_{10}$) | $\geq 5.7$ | $\geq 5.7$ | 7.0 |
| Virus reduction factor ($\log_{10}$) | $\geq 6.9$ | $\geq 5.6$ | 6.3 |

Validation of the Affinity Chromatography Step as a Virus Removal Step

The objective of this study was to determine the effectiveness (expressed as a reduction factor) of the affinity chromatography step of the production process measured as the removal of CPV (Canine parvo virus) and HAV (Hepatitis A virus), respectively, two small non-enveloped viruses of high physio-chemical resistance.

The effectiveness of this step was calculated by comparison of the measured amount of virus inoculated in the starting material and the recovery of virus in the material eluted from the column and expressed as the reduction factor. The reduction factors are summarized as follows:

| Affinity chromatography step | CPV | HAV |
| --- | --- | --- |
| Virus reduction factor ($\log_{10}$) | $3.8 \leq$ reduction $\leq 7.5$ | $3.2 \leq$ reduction $\leq 6.7$ |

REFERENCES

1. M. W. Turner, Immunology Today, 1996, 17, 532–540
2. H. J. Hoppe and K.B.M. Reid, Protein Sci, 1994, 3,1143–1158
3. M. Matsushita et al., Biochem Biophys Res Commun, 1992, 183, 645–651
4. S. Thiel et al., Nature, 1997, 386, 506–510
5. D. C. Kilpatrick et al., Hum Reproduc, 1995, 10, 2501–2505
6. Kawasaki, N., et al, J. Biochem (Tokyo), 1983, 94, 937–947
7. J. A. Summerfield and M.E. Taylor, Biochem Biophys Acta, 1986, 883, 197–206
8. J. Lu et al, J. Immunol, 1990, 144, 2287–2294
9. T. Kawasaki et al., Methods Enzymol, 1989, 179, 310–321
10. M. Kyogashima et al., Arch Biochem Biophys, 1990, 283, 217–222
11. S. M. Tan et al., Biochem J., 1996, 319, 329–332
12. E. Cohn et al., J Am Chem Soc, 1946,68, 459–475
13. P. Kistler and H.S. Nitschmann, Vox Sang, 1952, 7, 414–424

What is claimed is:

1. A process for purifying mannan-binding lectin (MBL) in a starting material, the process, comprising:
   performing an affinity chromatography step on a non-conjugated cross-linked polysaccharide matrix;
   performing a validated virus reduction step; and
   recovering MBL.

2. A process according to claim 1 wherein the starting material is an MBL containing supernatant, suspension, milk product, colostrum or crude plasma protein fraction.

3. A process according to claim 2, wherein the starting material is a crude plasma protein fraction.

4. A process according to claim 3, wherein the crude plasma protein fraction is a Cohn fraction.

5. A process according to any one of claims 1–4, wherein, prior to said affinity chromatography step more than 50% of immunoglobulins are eliminated from the starting material thereby recovering an MBL-containing protein fraction.

6. A process according to claim 1, wherein the buffer or buffers used for washing out protein contaminants from the affinity chromatography matrix after application of the MBL containing solution are non-denaturing and have a composition, pH, and ionic strength resulting in elimination of protein contaminants without elution of MBL.

7. A process according to claim 6, wherein one of the buffers is a Tris buffer with a content of Ca-ions of 0.2–2.0 mM.

8. A process according to claim 1, wherein the elution from the affinity chromatography matrix is performed with a selective desorbing agent in a neutral non-denaturing buffer.

9. A process according to claim 8, wherein the desorbing agent is a saccharide.

10. A process according to claim 8, wherein the desorbing agent is an agent chelating Ca-ions.

11. A process according to claim 1, wherein the affinity chromatography step serves as a virus removal step.

12. A process according to claim 1, wherein the virus reduction step is performed by adding a virucidal amount of a non-denaturing virus-inactivating agent to the MBL-containing solution resulting in a virus-safe MBL containing solution.

13. A process according to claim 12, wherein the non-denaturing virus-inactivating agent is a mixture of at least one non-denaturing detergent and at least one solvent.

14. A process according to claim 13, wherein the non-denaturing mixture of a non-ionic or ionic detergent and solvent is 0.8–1.5% detergent and 0.2–1.0% TNBP.

15. A process according to claim 1, wherein the final yield of MBL is more than 40% of the amount of MBL in the MBL containing solution applied to the affinity column.

16. A process according to claim 1, wherein the final MBL product is formulated by adding at least one protein stabilizer.

17. A process according to claim 1, wherein all steps are conducted under aseptic conditions.

18. A pharmaceutical formulation of a functionally active, oligomeric MBL plasma-derived product free from synthetic protease inhibitors and bacteriostatic agents.

19. An MBL product which is obtainable by the process according to claim 1.

20. A liquid MBL product according to claim 18.

21. A lyophilized MBL product according to claim 18.

22. An MBL product according to claim 18 with a concentration of at least 250 $\mu$g of MBL per ml.

23. An MBL product which is obtainable by the process according to claim 1 for use in medicine.

24. A method for the treatment of diseases associated with inherited or acquired MBL-deficiency in a mammal which comprises administering an effective MBL-deficiency treating amount of an MBL product according to claim 18.

25. The method according to claim 24, wherein the mammal is a human being.

26. The process according to claim 4, wherein said Cohn fraction is at least one member selected from the group consisting of Cohn fraction I, II and III.

27. A process according to claim 13, wherein the detergent is polysorbate 80.

28. A process according to claim 13, wherein the detergent is t-octylphenoxypolyethoxyethanol.

29. A process according to claim 13, wherein the solvent is dialkylphosphate.

30. A process according to claim 13, wherein the solvent is triakylphosphate.

* * * * *